(12) United States Patent
Jain et al.

(10) Patent No.: US 12,201,609 B2
(45) Date of Patent: Jan. 21, 2025

(54) SAROGLITAZAR FOR THE TREATMENT OF HEPATOCELLULAR CARCINOMA

(71) Applicant: CADILA HEALTHCARE LIMITED, Gujarat (IN)

(72) Inventors: Mukul R. Jain, Gujarat (IN); Suresh Giri, Gujarat (IN)

(73) Assignee: ZYDUS LIFESCIENCES LIMITED, Ahmedabad (IN)

( * ) Notice: Subject to any disclaimer, the term of this patent is extended or adjusted under 35 U.S.C. 154(b) by 772 days.

(21) Appl. No.: 17/414,733

(22) PCT Filed: Dec. 17, 2019

(86) PCT No.: PCT/IB2019/060898
§ 371 (c)(1),
(2) Date: Jun. 16, 2021

(87) PCT Pub. No.: WO2020/128815
PCT Pub. Date: Jun. 25, 2020

(65) Prior Publication Data
US 2022/0071954 A1 Mar. 10, 2022

(30) Foreign Application Priority Data
Dec. 18, 2018 (IN) .............. 201821047938

(51) Int. Cl.
*A61K 31/40* (2006.01)
*A61P 1/00* (2006.01)
*A61P 35/00* (2006.01)

(52) U.S. Cl.
CPC ............ *A61K 31/40* (2013.01); *A61P 35/00* (2018.01)

(58) Field of Classification Search
CPC ............ A61K 31/40; A61P 35/00; A61P 1/00
See application file for complete search history.

(56) References Cited

U.S. PATENT DOCUMENTS 9,814,697 B2 * 11/2017 Patel et al. ............. A61K 31/40

FOREIGN PATENT DOCUMENTS

| WO | 2003009841 | A1 | | 2/2003 | |
|----|----|----|----|----|----|
| WO | 2012/104869 | A1 | | 8/2012 | |
| WO | 2014174524 | A1 | | 10/2014 | |
| WO | WO2014174524 | | * | 10/2014 | ........... A61K 31/100 |
| WO | 2016181409 | A1 | | 11/2016 | |
| WO | 2017089979 | A1 | | 6/2017 | |
| WO | 2017089980 | A1 | | 6/2017 | |

OTHER PUBLICATIONS

Shen et al., (British Journal of Cancer (2012) 106, 1486-1494., PPAR gamma inhibits hepatocellular carcinoma metastases in vitro and in mice); (Year: 2012).*
Yu J, et al., Inhibitory role of peroxisome proliferator-activated receptor gamma in hepatocarcinogenesis in mice and in vitro; Hepatology (2010), 51: 2008-2019 (Year: 2010).*
Grommes et al., (Antineoplastic effects of peroxisome proliferator-activated receptor gamma agonists. Lancet Oncol. (2004), 5: 419-429 (Year: 2004).*
Yu J et al., (Troglitazone inhibits tumor growth in hepatocellular carcinoma in vitro and in vivo. Hepatology (2006), 43: 134-143 (Year: 2006).*
Yang et al (Molecular Carcinogenesis 54:1584-1595 (2015) (Year: 2015).*
Jain et al., (Liver International. 2018; 38:1084-1094., Dual PPARα/γ agonist Saroglitazar improves liver histopathology and biochemistry in experimental NASH models (Year: 2018).*
Bottoni et al., "A Two-Dimensional Electrophoresis Preliminary Approach to Human Hepatocarcinoma Differentiation Induced by PPAR-Agonists," Journal of Cellular and Molecular Medicine, vol. 9, No. 2, (2005), pp. 462-467, XP055685568, RO ISSN: 1582-1838, DOI: 10.1111/j. 1582-4934.2005.tb00371.
International Search Report for Application No. PCT/IB2019/060898; International Filing Date—Dec. 17, 2019; Date of Mailing—May 4, 2020; 4 pages.
Lindblom et al., "Tesaglitazar, A Dual PPAR-[alpha]/[gamma] Agonist, Hamster Carcinogenicity, Investigative Animal and Clinical Studies," Toxicologic Pathology, vol. 40, No. 1, (2011), pp. 18-32.
Tacke et al., "An Update on the Recent Advances in Antifibrotic Therapy," Expert Review of Gastroenterology and Hepatology, vol. 12, No. 11, (2018), pp. 1143-1152.
Written Opinion for Application No. PCT/IB2019/060898; International Filing Date—Dec. 17, 2019; Date of Mailing—May 4, 2020; 8 pages.
Yu et al., "Hepatobiliary Malignancies—Inhibitory Role of Peroxisome Proliferator-Activated Receptor Gamma in Hepatocarcinogenesis in Mice and InVitro," Hepatology, vol. 51, No. 6, (2010), pp. 2008-2019,.
Zydus Discovery: "Lipaglyn-Saroglitazar. Novel. Superior Dual Acting Product information," (2013), pp. 1-12, XP055685771, [retrieved on Apr. 15, 2020].
Kimura, O. et al.; "PPAR Could Contribute to the Pathogenesis of Hepatocellular Carcinoma"; PPAR Research, Vo. 2012, Article ID 574180; 5 pages; DOI: 10.1155/2012/574180 (2012).
Shen, Y-C. et al.; "Lack of efficacy of troglitazone at clinically achievable concentrations, with or without 9-cis retinoic acid or cytotoxic agents, for hepatocellular carcinoma cell lines"; British Journal of Cancer, vol. 91; pp. 1561-1565 (2004).

* cited by examiner

*Primary Examiner* — Bruck Kifle
(74) *Attorney, Agent, or Firm* — CANTOR COLBURN LLP

(57) ABSTRACT

The present invention relates to pharmaceutical compositions containing the formula (I) for the prevention, delay of progression, or treatment of a disease or condition from hepatocellular carcinoma. The present invention further provides the composition of formula (I) useful in the prevention and treatment of hepatocellular carcinoma.

6 Claims, 1 Drawing Sheet

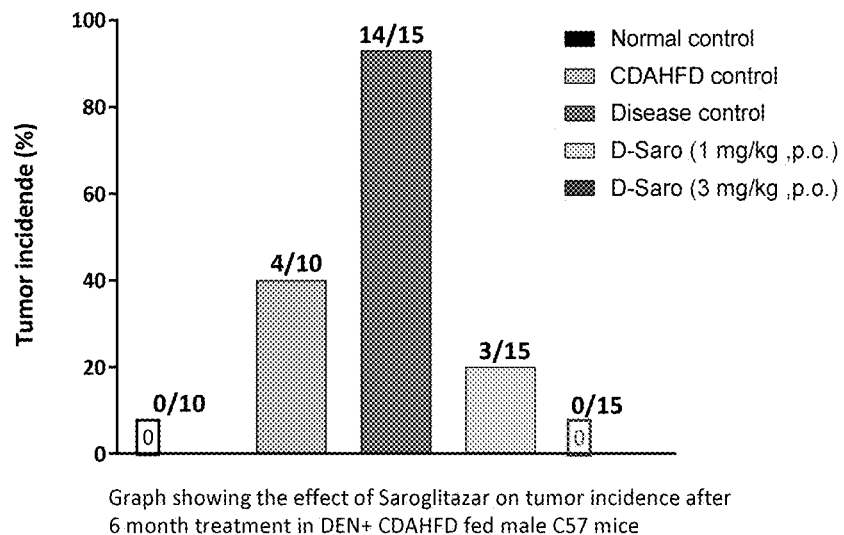
Figure 1. Percentage of animals with liver tumor
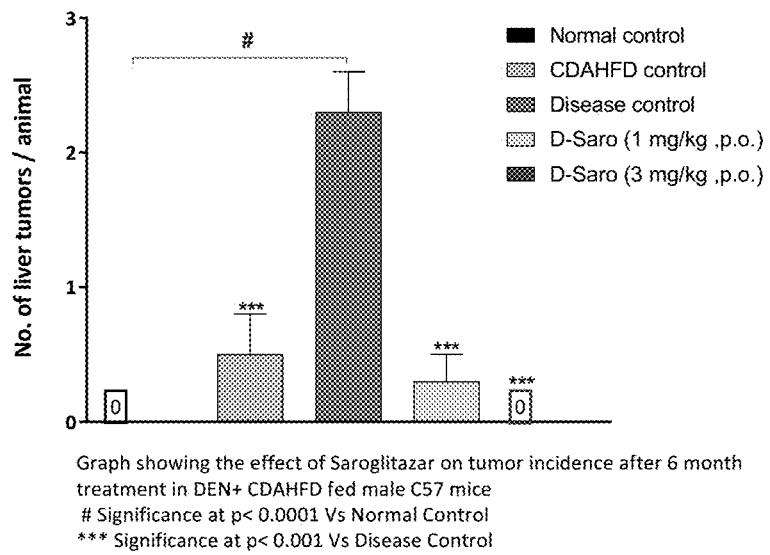
Figure 2. Number of tumors on liver

SAROGLITAZAR FOR THE TREATMENT OF HEPATOCELLULAR CARCINOMA

CROSS REFERENCE TO RELATED APPLICATIONS

This application is a National Stage application of PCT/IB2019/060898, filed Dec. 17, 2019, which claims priority to Indian application No. 201821047938, filed Dec. 18, 2018, the entire contents of which are hereby incorporated by reference.

FIELD OF THE INVENTION

The present invention relates to pharmaceutical compositions containing the formula (I) for the prevention, delay of progression, or treatment of a disease or condition from hepatocellular carcinoma. The present invention further provides the composition of formula (I) useful in the prevention and treatment of hepatocellular carcinoma.

BACKGROUND OF THE INVENTION

Hepatocellular carcinoma (HCC) is a primary malignancy of the liver and occurs predominantly in patients with underlying chronic liver disease and cirrhosis. According to the World Health Organization, HCC is the fifth most common tumor worldwide and the second most common cause of cancer-related death (http:/globocan.iarc.fr/old/FactSheets/cancers/liver-new.asp). The incidence of HCC has been rising rapidly in the United States over the last 20 years. According to estimates from the Surveillance Epidemiology End Results (SEER) program of the National Cancer Institute, the United States will have witnessed an estimated 39,230 cases of HCC and 27,170 HCC deaths in 2016 (https://seer.cancer.gov). In addition, a recent study using the SEER registry projects that the incidence of HCC will continue to rise until 2030.

There are various causes which develops hepatocellular carcinoma. Half of all cases of HCC are associated with hepatitis B virus infection, with a further 25% associated with hepatitis C virus. Other risk factors for developing HCC include alcoholic liver disease, cirrhosis, nonalcoholic steatohepatitis, intake of aflatoxin-contaminated food, diabetes, and obesity. (The Oncologist 2010; 15(suppl 4): 14-22).

Although most HCC occur in the setting of cirrhosis, up to 20% of affected patients have no underlying cirrhosis. Thus cirrhosis may not always be essential for development of HCC. Chronic viral hepatitis such as hepatitis B virus (HBV) or hepatitis C virus (HCV) and alcoholic liver disease are well-recognized causes of cirrhosis, while autoimmune hepatitis (AIH), primary biliary cirrhosis and NASH have, hitherto, occurred less commonly and thus have not been recognized as primary drivers for HCC (Int. J. Cancer, 2011: 128, 2436-2443). Two population based cohort studies in patients with NAFLD/NASH showed no increased incidence and 0.3% risk of HCC, respectively, over 6 years of follow up (Curr Med Res Opin. 2010; 26:2183-2191). Studies of NAFLD or NASH cohorts, with few or no cirrhosis cases, demonstrated a minimal HCC risk (cumulative HCC mortality between 0% and 3% for study periods up to two decades) [Hepatology. 2010; 51:595-602; Hepatol Res. 2012; 42:264-272] Similarly, a study published from Denmark that included biopsy proven NAFLD/NASH cases, but without significant fibrosis, found no increased risk of HCC when followed up for almost 21 years (Scand J Gastroenterol. 2009; 44:1236-1243). It is also showed that risk of HCC was lower in NAFLD-related cirrhosis as compared to its incidence in cirrhosis due to viral hepatitis (J Clin Gastroenterol. 2013 July; 47(0): S2-S6). Also it was reported in recent literature that, although there is high (~24%) prevalence of NAFLD in population, only a minority (incidence of 2.4-12.8%) will exhibit progressive liver disease into HCC or experience a liver-related death (Nature Reviews Gastroenterology & Hepatology, 2019:16, 411-428) and it is also not clear which of these patients will progress to HCC.

Various treatments are known for first and second line treatment for advanced HCC (Table 1 and Table 2 of Clinical Liver Disease, VOL 13, NO 1, January 2019). Currently, there is no established therapy for patients suffering from HCC. So, there is a need to provide effective treatment or chemoprevention for hepatocellular carcinoma.

WO 03009841 discloses compounds of the following general formula (A)

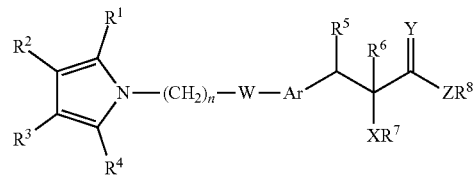

(A)

These compounds are reported as a hypolipidaemic agent. This document also discloses sodium and calcium salts of some of the compounds disclosed therein.

WO 2012/104869 discloses Saroglitazar (I) and its Magnesium salt being effective in the treatment of lipohypertrophy, lipoatrophy and metabolic abnormalities in HIV patients.

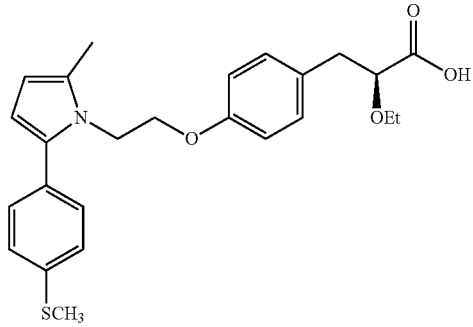

(I)

WO 2014/174524 discloses the use of Saroglitazar (I) and its pharmaceutically acceptable salts for the treatment of Non-alcoholic Fatty Liver Diseases (NAFLD) & Non-alcoholic Steatohepatitis (NASH).

WO 2016/181409 discloses the use of Saroglitazar and its pharmaceutically acceptable salts for the treatment of Chylomicronemia.

WO 2017/089979 discloses the use of the compound (I) and its pharmaceutically acceptable salts for the treatment of Nephropathy.

WO 2017/089980 discloses the use of the compound (I) and its pharmaceutically acceptable salts for the treatment of retinopathy.

Disclosed herein are the use of the compound (I) and its pharmaceutically acceptable salts for the treatment of Hepatocellular Carcinoma.

OBJECTIVE OF THE INVENTION

In one embodiment, the present invention discloses a pharmaceutical composition containing the compound of Formula (I)

Formula (I)

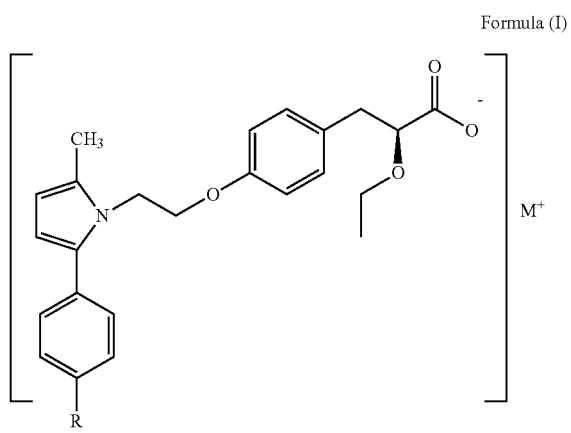

for the prevention, delay of progression, or treatment of a disease or condition from hepatocellular carcinoma.

In another embodiment the present invention provides a method and a formulation comprising an effective amount of compound of Formula (I) for treating hepatocellular carcinoma.

The method comprises administering to a subject an effective amount of a compound of formula (I) as a pharmaceutical formulation, as disclosed hereinafter including pharmaceutically acceptable salts of the compound of formula (I).

In yet another embodiments the invention further provides a pharmaceutical composition containing effective amount of compound of formula (I) suitable for treatment of hepatocellular carcinoma.

In another embodiment the present invention provides a method of treating hepatocellular carcinoma in a subject, comprising administering to the subject an effective amount of a compound according to Formula (I), or a pharmaceutically acceptable salt thereof as a suitable pharmaceutically acceptable composition.

In another embodiment the present invention provides a method of treating hepatocellular carcinoma comprising administering to the subject an effective amount of a compound according to Formula (I), or a pharmaceutically acceptable salt thereof. The above and other embodiments of the present invention are disclosed further hereinafter.

BRIEF DESCRIPTION OF THE ACCOMPANYING FIGURES

FIG. 1: Effect of magnesium salt of compound of formula (I) wherein R is —SMe on tumor incidence (Percentage of animals with Liver Tumor)

FIG. 2: Effect of magnesium salt of compound of formula (I) wherein R is —SMe on tumor incidence (Number of tumors on liver)

DETAIL DESCRIPTION OF THE INVENTION

The present invention describes a pharmaceutical composition for treating and preventing certain diseases and conditions in subject suffering from hepatocellular carcinoma and methods for ameliorating and/or treating such disease conditions.

The formulation comprises compound of formula (I) and the method comprises administering to a subject in need thereof an effective amount of a compound according to Formula (I), or a pharmaceutically acceptable salt thereof.

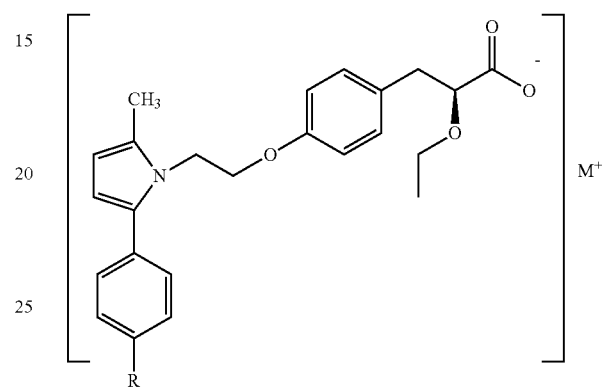

wherein 'R' is selected from hydroxy, hydroxyalkyl, acyl, alkoxy, alkylthio, thioalkyl, aryloxy, arylthio and M$^+$ represents suitable metal cations such as Na$^+$, K$^+$, Ca$^{+2}$, Mg$^{+2}$ and the like.

Definitions and Abbreviations

As used above, and throughout this disclosure, the following terms, unless otherwise indicated, shall be understood to have the following meanings:

"Patient" includes both human and animals.

"Mammal" means humans and other mammalian animals.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, one or more of the following results: partially or totally reducing the extent of the disease, disorder or syndrome (e.g., reducing fat deposits, increasing insulin activity/sensitivity, reducing weight); ameliorating or improving a clinical symptom or indicator associated with the disorder; delaying, inhibiting or preventing the progression of the disease, disorder or syndrome; or partially or totally delaying, inhibiting or preventing the onset or development of disorder. Delaying, inhibiting or preventing the progression of the disease, disorder or syndrome includes for example, delaying, inhibiting or preventing the progression of HCC.

The term "alkyl" used herein, either alone or in combination with other radicals, denotes a linear or branched radical containing one to twelve carbons, such as methyl, ethyl, n-propyl, iso-propyl, n-butyl, sec-butyl, tert-butyl, amyl, t-amyl, n-pentyl, n-hexyl, iso-hexyl, heptyl, octyl and the like.

The term "alkoxy" used herein, either alone or in combination with other radicals, denotes a radical alkyl, as defined above, attached directly to an oxygen atom, such as methoxy, ethoxy, n-propoxy, iso-propoxy, n-butoxy, t-butoxy, iso-butoxy, pentyloxy, hexyloxy, and the like.

The term "aryl" or "aromatic" used herein, either alone or in combination with other radicals, refers to an optionally substituted aromatic system containing one, two or three rings wherein such rings may be attached together in a pendant manner or may be fused, such as phenyl, naphthyl, tetrahydronaphthyl, indane, biphenyl, and the like. The term "aralkyl" denotes an alkyl group, as defined above, attached to an aryl, such as benzyl, phenethyl, naphthylmethyl, and the like. The term "aryloxy" denotes an aryl radical, as defined above, attached to an alkoxy group, such as phenoxy, naphthyloxy and the like, which may be substituted. The term "aralkoxy" denotes an arylalkyl moiety, as defined above, such as benzyloxy, phenethyloxy, naphthylmethyloxy, phenylpropyloxy, and the like, which may be substituted.

The term "acyl" used herein, either alone or in combination with other radicals, refers to a radical containing one to eight carbons such as formyl, acetyl, propanoyl, butanoyl, iso-butanoyl, pentanoyl, hexanoyl, heptanoyl, benzoyl and the like, which may be substituted.

The term "hydroxyalkyl" used herein, either alone or in combination with other radicals, refers to an alkyl group, as defined above, substituted with one or more hydroxy radicals, such as hydroxymethyl, hydroxyethyl, hydroxypropyl, hydroxybutyl, hydroxypentyl, hydroxyhexyl and the like.

The term "thio($C_1$-$C_{12}$)alkyl" or "thio(($C_1$-$C_6$)alkyl" used herein, either alone or in combination with other radicals, represents an alkyl group, as defined above, attached to a group of formula —SR', where R' represents hydrogen, alkyl or aryl group, e.g. thiomethyl, methylthiomethyl, phenylthiomethyl and the like, which may be substituted One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates.

One or more compounds of the invention may optionally be converted to a solvate. Preparation of solvates is generally known. Thus, for example, M. Caira et al, J. Pharmaceutical Sci, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001)

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contain both a basic moiety, such as, but not limited to a pyridine or imidazole, and an acidic moiety, such as, but not limited to a carboxylic acid, zwitterions ("inner salts") may be formed and are also included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula I with an amount of acid or base, such as an equivalent amount, in a medium such as one in which the salt precipitates or in an aqueous medium followed by lyophilization.

Polymorphic forms of the compounds of Formula (I), and of the salts, solvates, esters and prodrugs of the compounds of Formula (I) are intended to be included in the present invention.

As used herein, the term "composition" is intended to encompass a product comprising the specified ingredients in the specified amounts, as well as any product which results, directly or indirectly, from combination of the specified ingredients in the specified amounts.

In an embodiment the compound according to formula (I) or its pharmaceutically acceptable salts can be used alone or in combination e.g., as an adjunct therapy, with at least one other therapeutic agent. Compounds according to formula (I) or its pharmaceutically acceptable salts can be given to a subject with HCC alone, or can be co-administered with a therapeutic agent including a beta adrenergic receptor antagonist such as propranolol or its derivatives, non-steroidal anti-inflammatory drug (a NSAID) such as a cyclooxygenase (COX) (or a prostaglandin synthase) inhibitor, the COX inhibitor of wherein the COX inhibitor is selected from etodolac, naproxen, celecoxib, rofecoxib, etoricoxib, valdecoxib, parecoxib, nabumetone, diclofenac (2-(2,6-dichloranilino) phenylacetic acid) or lumiracoxib; Angiogenesis inhibitors such as Sorafenib, regorafenib Rugorafenib, lenvatinib; m-TOR inhibitor such as Everolimus or Rapamycin; VEGFR2 receptor such as Cabozatinib; anti-cancer or anti-tumor antibody such as alemtuzumab, brentuximab vetting, cetuximab, agemtuzumab ozogamicin, abritumomab tiuxetan, nimotuzumab, nivolumab, pembrolizumab of atumumab, panitumumab, rituximab, tositumomab, or trastuzumab; interferon (IFN) such as recombinant IL-2, aldesleukin, proleukin; chemotherapeutic agent such as doxorubicin or a carboplatin; statin such as Pitavastatin, Atorvastatin, Rosuvastatin; Gemcitabine, Capecitabine; alkylating agent such as Temozolomide, Cisplatin, Carboplatin, Oxaloplatin or Cyclophosphamide; a nucleoside or nucleotide analog, a topoisomerase inhibitor; a glycopeptide antibiotic; steroid receptor inhibitor; a mitochondrial inhibitor phenformin; a small-molecule multikinase inhibitor such as Sunitinib, Cabozantinib; a matrix metalloproteinase (MMP) inhibitor; a macrolide or a composition comprising a macrolide ring or direct acting antiviral agent Sofosbuvir, daclatasvir.

In the embodiments the present invention provides a suitable pharmaceutical composition of compounds of formula (I) or its pharmaceutically acceptable salts, which comprises one or more pharmaceutical excipients, antioxidants and chelating agents, wherein the pH of the composition is above 6, preferably in the range from about pH 6 to pH of about 10.

In such embodiments the pharmaceutical composition of the present invention essentially comprises of:
    the pharmaceutically active substance;
    suitable additive agent
    a suitable stabilizer;
    optionally with one or more pharmaceutically acceptable excipients.

Each of the components may be selected from those known in the art.

In an embodiment suitable stabilizers may be selected from the classes of antioxidants or chelating agents.

In an embodiment the pharmaceutical excepients according to the present invention can be selected from solubilizers, diluents, fillers, disintegrants, binder, lubricants, glidants, wetting agents, solvents and the like as is known in the art.

In an embodiment suitable additives are selected from sodium benzoate, sodium hydroxide, sodium sulfite and sodium carbonate.

In an embodiment antioxidants used according to the present invention include, but are not limited to citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), and propyl gallate and combinations thereof and other similar material known to those of ordinary skilled in the art.

Chelating agent used according to the present invention include, but are not limited to Disodium EDTA, citric acid and or its salts, maleic acid, chlorambutol, chlorhexidine or its salts, chlorocresol, combinations thereof and other similar material known to those of ordinary skill in the art.

As used herein, the term "binders" is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methyl cellulose, povidone and pregelatinized starch, combinations thereof and other similar material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC F68, PLURONIC F127), collagen, albumin, celluloses in non-aqueous solvents, and the like or their suitable combinations. Other binders which may be included may be, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "glidant" is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

In an embodiment, the term "lubricant" is intended to mean substances used in tablet formulations to reduce friction during tablet compression. Such compounds include, by way of example and without limitation, calcium stearate, magnesium stearate, mineral oil, stearic acid, zinc stearate, suitable combinations thereof and other such materials known to those of ordinary skill in the art.

In an embodiment, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

In an embodiment, the term "wetting agent" is intended to mean a compound used to aid in attaining intimate contact between solid particles and liquids. Exemplary wetting agents include, by way of example and without limitation, poloxamers, gelatin, casein, Glycerol mono-oleate, lecithin (phosphatides), gum acacia, cholesterol, tragacanth, stearic acid, benzalkonium chloride, calcium stearate, glycerol monostearate, cetostearyl alcohol, sodium lauryl sulphate, sodium dodecyl sulfate, salts of bile acids (taurocholate, glycocholate, cholate, deoxycholate, etc.), cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN), polyethylene glycols, polyoxyethylene stearates colloidal silicon dioxide, phosphates, sodium dodecyl sulfate, carboxymethylcellulose calcium, carboxy methylcellulosesodium, methyl cellulose, hydroxy ethyl cellulose, hydroxylpropylcellulose, hydroxy propyl methyl cellulose phthalate, noncrystalline cellulose, magnesium aluminum silicate, triethanolamine, polyvinyl alcohol, and poly vinyl pyrrolidone (PVP) & their suitable combinations and other such materials known to those of ordinary skill in the art. Tyloxapol (a nonionic liquid polymer of the alkyl aryl polyether alcohol type, also known as superinone or triton) is another useful wetting agent which may be used. In another embodiment of the present invention, is a described process for the preparation of a stable pharmaceutical composition of compounds of formula (I) or their derivatives.

The stable pharmaceutical composition may be made by direct compression, wet granulation or dry granulation methods by techniques known to persons skilled in the art. Thus, for example, In wet granulation process, the drug is mixed with one or more pharmaceutical excepients and granulated with suitable binding solution as described earlier, to form wet granules, the wet granules are dried and optionally sieved. The dried granules are mixed with one or more suitable excipients from those described elsewhere and then compressed into tablets or filled into capsules.

In direct compression process, the drug is mixed with all the pharmaceutical excipients required and then is either compressed into tablets or filled in capsules.

In dry granulation process the drug is mixed with one or more pharmaceutical excipients and compressed into slugs and these slugs are passed through required sieve. The sieved granules are mixed with one or more suitable excipients from those described elsewhere and then compressed into tablets or filled into capsules.

One or more solvents used in the formulation are selected from acetone, chloroform, dichloromethane, ethyl alcohol, ethyl acetate, methyl alcohol, isopropyl alcohol and combinations thereof and other such materials known to those of ordinary skill in the art.

In an embodiment, the compound of formula (I) or pharmaceutical compositions containing the compound of formula (I) is given to a subject in need thereof at a dose of about 0.5 mg to 5 g. A skilled person is aware how to decide the optimum dose based on the patient profile, the severity of disease, the presence of secondary medicines and the like.

The present invention further discloses use of said compound of formula (I) or their suitable pharmaceutical compositions for the treatment of Hepatocelolular Carcinoma.

The compound of formula (I), when R is —SMe and $M^+$ is Mg, is dosed to patients in need thereof for the treatment of Hepatocellular carcinoma as per the following study:

Evaluation of Saroglitazar's efficacy in Hepatocellular Carcinoma Induced by Intraperitoneal Injection of Diethylnitrosamine in C57/BL6 Mice.

In this study, hepatocellular carcinoma (HCC) was induced in C57BL/6 male mice first by injecting them with diethylnitrosamine (DEN) and by then feeding them a choline-deficient, L-amino acid-defined, high-fat diet (CDAHFD); Developed an experimental mouse model of hepatocellular carcinoma (Ohno T, Shimizu M, Shirakami Y, Baba A, Kochi T, Kubota M, et al. (2015) Metformin Suppresses Diethylnitrosamine-Induced Liver Tumorigenesis in Obese and Diabetic C57BL/KsJ-+Leprdb/+Leprdb Mice. PLoS ONE 10(4): e0124081; Journal of Cancer, 2018; 9(5): 914-922;)

Purpose

The objective of this study was to evaluate the efficacy of Saroglitazar for prevention and or regression of hepatocellular carcinoma in mice after intraperitoneal injection of diethylnitrosamine and feeding of Choline deficient, L-amino acid-defined, High-fat Diet.

Methods

HCC was induced in C57BL/6 male mice by feeding them a choline-deficient, L-amino acid-defined, high-fat diet (CDAHFD) and administration of diethylnitrosamine (DEN). DEN was administered one-time by intraperitoneal route at the age of 3-weeks. Treatment with Saroglitazar (1 and 3 mg/kg) was initiated after 8 weeks of CDAHFD initiation and continued for 27 weeks.

After 8 weeks of CDAHFD diet (or DEN administration) blood collection was performed for serum ALT, AST and on the basis serum ALT level animals were divided in to following groups:
1. Control for CDAHFD+Vehicle (n=10)—Normal Control
2. CDAHFD—Saline+Vehicle (n=10)—CDAHFD Control
3. CDAHFD—DEN+Vehicle (n=15)—Disease Control
4. CDAHFD—DEN+Saroglitazar 1 mg/kg, p.o. (n=15)—D-Saro (1 mg/kg, p.o.)
5. CDAHFD—DEN+Saroglitazar 3 mg/kg, p.o. (n=15)—D-Saro (3 mg/kg, p.o.)

Test compound formulation was prepared in Tween 80 and 0.5% sodium CMC in ratio of 0.5:99.5 in such that volume of administration will be 10 ml/kg.

Treatment along with diet was continued for 27 weeks.

In this study almost 50% animals from each group were terminated at 31 weeks after DEN injection and remaining 50% animals were sacrificed at 35 weeks after DEN administration (i.e. completion of 27 weeks of treatment). At termination, blood collection was performed for serum parameters like ALT, AST and TG. Animals were sacrificed; spleen and liver will be collected and weighed. Liver will be observed for presence of tumors, number of tumors and size of tumors. Liver was collected for liver biochemistry, histology Results 1. The mice which were injected with DEN and fed with CDAHFD (Disease control) group showed 93% of liver tumor incidence, i.e. all fifteen animals except one (14/15) showed liver tumors and each animals showed 2-3 tumors in liver. The animals treated with Saroglitazar showed dose dependent effect on liver tumor incidence and animals treated with saroglitazar 3 mg/kg dose did not show any tumor in liver indicating 100% prevention of hepatic carcinogenesis (Table 1 & 2 and FIGS. 1 and 2).
2. The animals of disease control group showed 6 and 5-fold increase in serum ALT and AST levels and saroglitazar (3 mg/kg) treatment has shown 40 and 44% reduction in serum liver injury markers (ALT and AST) respectively. Saroglitazar also shown dose dependent reduction in serum triglycerides levels (Table no. 3)

TABLE 1

Effect on liver tumor observed

| Sr. no | Treatment | No. of animal with tumor | % animals showing liver tumor |
|---|---|---|---|
| 1 | Control for CDAHFD + Vehicle | 0 out of 10 | 0.0 |
| 2 | CDAHFD – Saline + Vehicle | 4 out of 10 | 40.0 |
| 3 | CDAHFD – DEN + Vehicle (Disease Control) | 14 out of 15 | 93.3 |
| 4 | CDAHFD – DEN + Saroglitazar 1 mg/kg, p.o. | 3 out of 15 | 20.0 |
| 5 | CDAHFD – DEN + Saroglitazar 3 mg/kg, p.o. | 0 out of 15 | 0.0 |

TABLE 2

Average number of liver tumors observed per animals

| Sr. no | Treatment | No. of liver tumors/animal |
|---|---|---|
| 1 | Control for CDAHFD + Vehicle | 0.0 ± 0.0 |
| 2 | CDAHFD – Saline + Vehicle | 0.7 ± 0.4 |
| 3 | CDAHFD – DEN + Vehicle (Disease Control) | 2.3 ± 0.3 |
| 4 | CDAHFD – DEN + Saroglitazar 1 mg/kg, p.o. | 0.3 ± 0.2 |
| 5 | CDAHFD – DEN + Saroglitazar 3 mg/kg, p.o. | 0.0 ± 0.0 |

TABLE 3

Effect on serum biochemical parameters

Serum ALT levels (U/L)

| Sr. no | Treatment Group | Serum ALT levels (U/L) | % Change Vs Disease Control |
|---|---|---|---|
| 1 | Control for CDAHFD + Vehicle | 54.8 ± 8.1 | |
| 2 | CDAHFD – Saline + Vehicle | 342.6 ± 30.6 | |
| 3 | CDAHFD – DEN + Vehicle (Disease Control) | 350.1 ± 35.4 | |
| 4 | CDAHFD – DEN + Saroglitazar 1 mg/kg, p.o. | 232.3 ± 36.9 | −33.6 ± 10.5 |

TABLE 3-continued

Effect on serum biochemical parameters

| | | | | | | | |
|---|---|---|---|---|---|---|---|
| 5 | CDAHFD – DEN + Saroglitazar 3 mg/kg, p.o. | 210.5 | ± | 31.4 | −39.9 | ± | 9.0 |

Serum AST levels (U/L)

| Sr. no | Treatment Group | Serum AST levels (U/L) | | | % Change Vs Disease Control | | |
|---|---|---|---|---|---|---|---|
| 1 | Control for CDAHFD + Vehicle | 74.8 | ± | 6.0 | | | |
| 2 | CDAHFD – Saline + Vehicle | 335.8 | ± | 33.1 | | | |
| 3 | CDAHFD – DEN + Vehicle (Disease Control) | 362.2 | ± | 36.7 | | | |
| 4 | CDAHFD – DEN + Saroglitazar 1 mg/kg, p.o. | 231.1 | ± | 29.1 | −36.2 | ± | 8.0 |
| 5 | CDAHFD – DEN + Saroglitazar 3 mg/kg, p.o. | 203.0 | ± | 23.8 | −43.9 | ± | 6.6 |

Serum TG levels (mg/dl)

| Sr. no | Treatment Group | Serum TG levels (mg/dl) | | | % Change Vs Disease Control | | |
|---|---|---|---|---|---|---|---|
| 1 | Control for CDAHFD + Vehicle | 74.0 | ± | 4.9 | | | |
| 2 | CDAHFD – Saline + Vehicle | 68.7 | ± | 3.8 | | | |
| 3 | CDAHFD – DEN + Vehicle (Disease Control) | 69.4 | ± | 5.2 | | | |
| 4 | CDAHFD – DEN + Saroglitazar 1 mg/kg, p.o. | 42.7 | ± | 3.1 | −38.4 | ± | 4.5 |
| 5 | CDAHFD – DEN + Saroglitazar 3 mg/kg, p.o. | 31.5 | ± | 3.6 | −54.6 | ± | 5.2 |

CONCLUSION

In conclusion, Saroglitazar treatment showed significant reduction in liver injury markers, serum ALT and AST. Almost all control animals showed liver tumors whereas saroglitazar (3 mg/kg)-treated animals did not show any tumor in liver indicating 100% prevention of hepatic carcinogenesis. The data suggests that Saroglitazar prevents liver tumorigenesis and can be a potent candidate for chemoprevention of liver tumorigenesis.

We claim:

1. A method of treating Hepatocellular Carcinoma, comprising administering to a patient in need thereof a therapeutically effective amount of a pharmaceutical composition comprising a pharmaceutically acceptable salt of

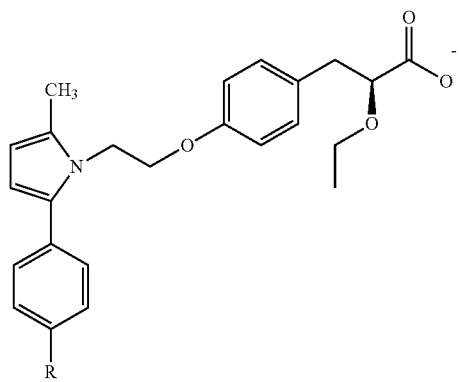

wherein R is —S-methyl, to treat the Hepatocellular Carcinoma.

2. The method of claim 1, wherein the pharmaceutically acceptable salt is a metal cation salt.

3. The method of claim 1, wherein the pharmaceutically acceptable salt is a metal cation salt selected from the group consisting of a sodium salt, potassium salt, calcium salt, and magnesium salt.

4. The method of claim 1, wherein the pharmaceutically acceptable salt is a magnesium salt.

5. A method of treating Hepatocellular Carcinoma, comprising administering to a patient in need thereof a therapeutically effective amount of a pharmaceutical composition comprising a pharmaceutically acceptable excipient and compound of Formula (I)

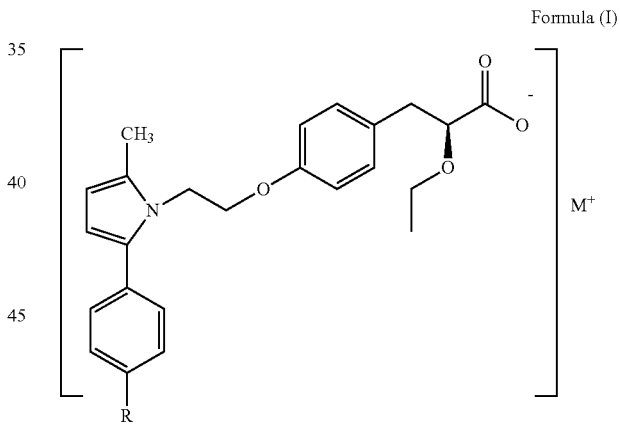

Formula (I)

wherein R is —S-methyl and $M^+$ is a metal cation, to treat the Hepatocellular Carcinoma.

6. The method of claim 5, wherein $M^+$ is $Mg^{2+}$.

* * * * *